US010379116B2

(12) United States Patent
Tan et al.

(10) Patent No.: US 10,379,116 B2
(45) Date of Patent: *Aug. 13, 2019

(54) DETECTION SYSTEM FOR HIGH SENSITIVITY FLUORESCENT ASSAYS

(71) Applicant: Access Medical Systems, LTD., Palo Alto, CA (US)

(72) Inventors: Hong Tan, San Jose, CA (US); Robert F. Zuk, Menlo Park, CA (US); Yushan Tan, Shanghai (CN); Erhua Cao, Shanghai (CN); Min Xia, Shanghai (CN); Jun Chen, Shanghai (CN)

(73) Assignee: Access Medical Systems, LTD., Palo Alto, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 15/256,319

(22) Filed: Sep. 2, 2016

(65) Prior Publication Data

US 2016/0370363 A1  Dec. 22, 2016

Related U.S. Application Data

(60) Continuation of application No. 13/846,517, filed on Mar. 18, 2013, now Pat. No. 9,434,789, which is a (Continued)

(51) Int. Cl.
| *G01N 33/543* | (2006.01) |
| *G01N 21/64* | (2006.01) |
| *C08B 37/00* | (2006.01) |

(52) U.S. Cl.
CPC ..... *G01N 33/54366* (2013.01); *C08B 37/006* (2013.01); *G01N 21/645* (2013.01);
(Continued)

(58) Field of Classification Search
CPC ....... G01N 33/54356; G01N 33/54373; G01N 21/6428; G01N 21/645
(Continued)

(56) References Cited

U.S. PATENT DOCUMENTS

| 3,300,474 A | 1/1967 | Gustaf et al. |
| 3,996,345 A | 12/1976 | Ullman et al. |

(Continued)

FOREIGN PATENT DOCUMENTS

| CA | 2497555 A1 | 4/2004 |
| CN | 2559982 Y | 7/2003 |

(Continued)

OTHER PUBLICATIONS

Extended European Search Report dated Jul. 30, 2012 for Application No. EP10749212.
(Continued)

*Primary Examiner* — David P Porta
*Assistant Examiner* — Meenakshi S Sahu
(74) *Attorney, Agent, or Firm* — Perkins Coie LLP; Viola T. Kung

(57) ABSTRACT

This invention relates to a detection system for measuring a fluorescent signal in a fluorescent assay. The system comprises a probe having a small sensing surface bound with a fluorescent label, and a light source and a detector both mounted at the proximal side of the sensing surface of the substrate. The invention also relates to a method for detecting an analyte in a liquid sample using a probe tip having a small surface area (≤5 mm) and a high molecular weight polymer (≥1 MD) having multiple binding molecules and multiple fluorescent labels. The binding reaction is accelerated by flowing the reaction solutions laterally and moving the probe tip up and down in the reaction vessels. The invention furthers relates to a fluorescent labeling compo- (Continued)

sition comprising a cross-linked FICOLL® molecule having a plurality of binding molecules and a plurality of fluorescent labels.

11 Claims, 13 Drawing Sheets

Related U.S. Application Data continuation of application No. 13/653,362, filed on Oct. 16, 2012, now Pat. No. 8,415,172, which is a division of application No. 13/224,174, filed on Sep. 1, 2011, now Pat. No. 8,309,369, which is a continuation of application No. PCT/US2010/025938, filed on Mar. 2, 2010.

(60) Provisional application No. 61/303,567, filed on Feb. 11, 2010, provisional application No. 61/299,525, filed on Jan. 29, 2010, provisional application No. 61/209,116, filed on Mar. 3, 2009.

(52) U.S. Cl.
CPC ... *G01N 21/6428* (2013.01); *G01N 33/54373* (2013.01); *G01N 2021/6439* (2013.01); *G01N 2201/06113* (2013.01)

(58) Field of Classification Search
USPC ...................................................... 250/461.1
See application file for complete search history.

(56) References Cited

U.S. PATENT DOCUMENTS

| | | | |
|---|---|---|---|
| 4,200,613 A | 4/1980 | Alfrey et al. | |
| 4,208,479 A | 6/1980 | Zuk et al. | |
| 4,272,510 A | 6/1981 | Smith et al. | |
| 4,276,259 A | 6/1981 | Eibl et al. | |
| 4,434,150 A | 2/1984 | Azad et al. | |
| 4,447,546 A * | 5/1984 | Hirschfeld | G01N 21/6428 250/227.11 |
| 4,483,925 A | 11/1984 | Noack | |
| 4,599,315 A | 7/1986 | Terasaki et al. | |
| 4,778,751 A | 10/1988 | El Shami et al. | |
| 4,822,565 A | 4/1989 | Kohler | |
| 4,886,787 A | 12/1989 | de Belder et al. | |
| 4,891,321 A | 1/1990 | Hubscher | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,320,814 A | 6/1994 | Walt et al. | |
| 5,449,625 A | 9/1995 | Kobayashi et al. | |
| 5,486,616 A | 1/1996 | Waggoner et al. | |
| 5,494,830 A | 2/1996 | Hubscher | |
| 5,650,334 A | 7/1997 | Zuk et al. | |
| 5,814,524 A | 9/1998 | Walt et al. | |
| 6,146,593 A | 11/2000 | Pinkel et al. | |
| 6,197,597 B1 | 3/2001 | Tuunanen | |
| 6,210,910 B1 | 4/2001 | Walt et al. | |
| 6,667,159 B1 | 12/2003 | Walt et al. | |
| 8,492,139 B2 * | 7/2013 | Tan | G01N 21/645 422/82.11 |
| 2005/0106724 A1 | 5/2005 | Schierholz et al. | |
| 2010/0062544 A1 | 3/2010 | Evans et al. | |

FOREIGN PATENT DOCUMENTS

| | | |
|---|---|---|
| CN | 1434287 A | 8/2003 |
| CN | 101118216 A | 2/2008 |
| JP | 1993(H05)-005742 A | 1/1993 |
| JP | 2002236223 A | 8/2002 |
| JP | 2002-257732 | 9/2002 |
| JP | 2004-271433 | 9/2004 |
| WO | 1995/30148 A1 | 11/1995 |
| WO | 1997/08552 | 3/1997 |
| WO | 2002/054067 A2 | 7/2002 |
| WO | 2008/127779 | 10/2008 |

OTHER PUBLICATIONS

International Search Report for International Application No. PCT/US2010/025938 dated Oct. 13, 2010.
Wang, et al., (Journal of Chromatography A, 800 (1998) 181-185).

* cited by examiner

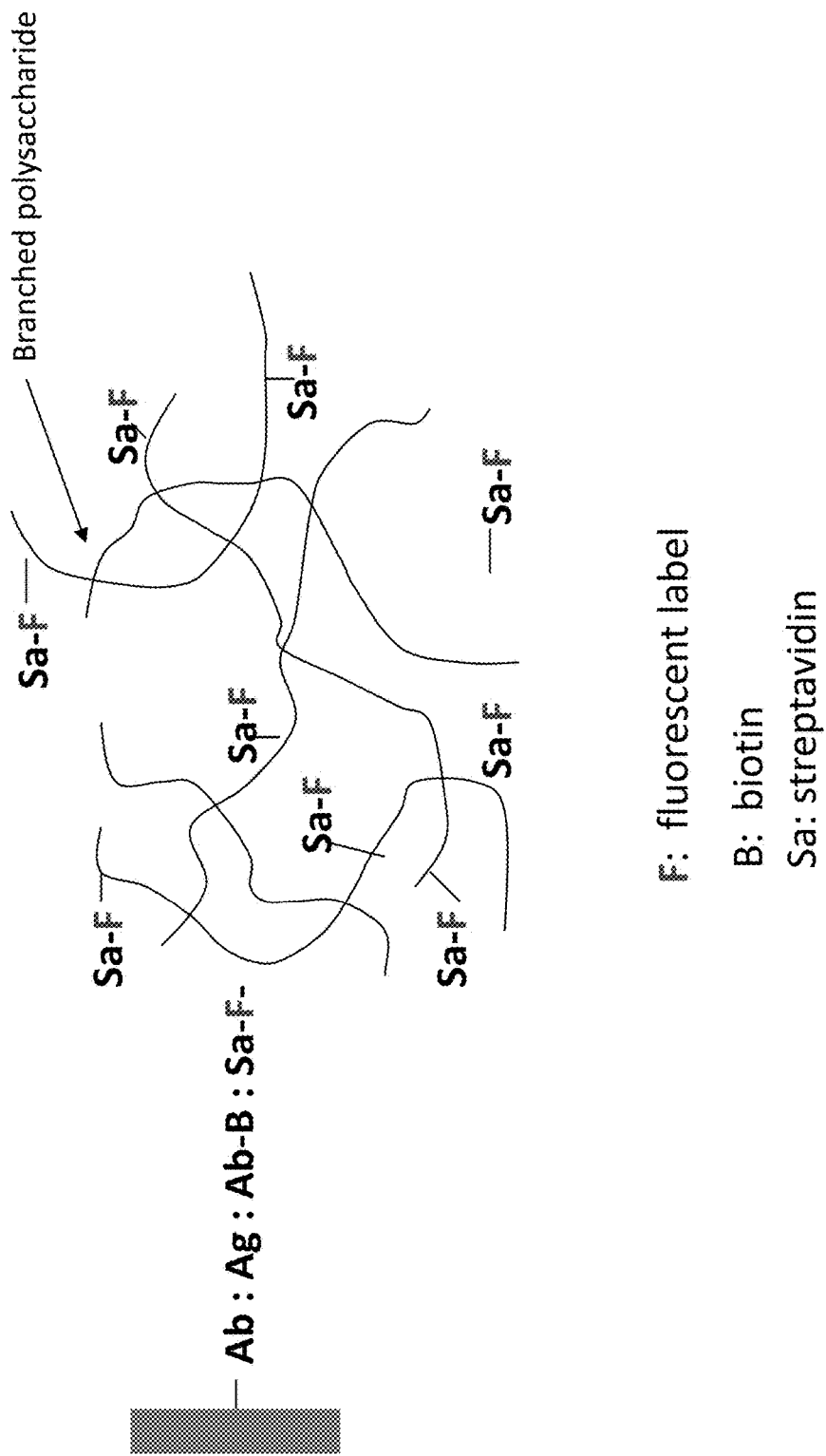

DETECTION SYSTEM FOR HIGH SENSITIVITY FLUORESCENT ASSAYS

This application is a continuation of U.S. patent application Ser. No. 13/846,517, filed Mar. 18, 2013; which is a continuation of U.S. application Ser. No. 13/653,362, filed Oct. 16, 2012, now U.S. Pat. No. 8,415,172; which is a divisional of U.S. application Ser. No. 13/224,174, filed Sep. 1, 2011, now U.S. Pat. No. 8,309,369; which is a continuation of PCT/US2010/025938, filed Mar. 2, 2010; which claims the priority of U.S. Provisional Application No. 61/209,116, filed Mar. 3, 2009; 61/299,525, filed Jan. 29, 2010, and 61/303,567, filed Feb. 11, 2010. The contents of the above-identified applications are incorporated herein by reference in their entirety.

FIELD OF THE INVENTION

This invention relates to a detection system for measuring a fluorescent signal in a fluorescent assay. The system comprises a probe having a sensing surface bound with a fluorescent label, and a light source and a detector both mounted at the proximal side of the sensing surface of the substrate. The invention also relates to a method for detecting an analyte in a liquid sample using a probe having a small surface and a polymer having multiple binding molecules and multiple fluorescent labels. The invention furthers relates to a fluorescent labeling composition comprising a cross-linked polysaccharide backbone molecule having a plurality of binding molecules and a plurality of fluorescent labels.

BACKGROUND OF THE INVENTION

In the development of immunoassay systems, many performance requirements need be met. Assays need be sensitive enough to detect analyte at very low levels in the subpicogram nanogram range. Total assay time needs to be 15 minutes or less in order to provide timely results for patient management in point of care situations, or to meet throughput requirements for batch analyzers. In some cases, analyte panels where multiple assays are simultaneously performed with the same sample are advantageous in order to minimize the turnaround time for results and test costs.

Many immunoassays employ fluorescent labels because such labels offer many practical advantages. Compared to enzymes, fluorescent labels are much more stable and do not require an additional substrate reagent. For multianalyte panels, fluorescent labels enable the use of discrete binding zones within a common reaction chamber since each binding zone can be sequentially subjected to fluorescence excitation and emission measurements without interference from adjacent binding zones. Assays utilizing fluorescent labels, however, are less sensitive than enzyme based assays primarily due to the enzyme's ability to catalytically convert substrate to accumulate a great amount of product molecules over time.

Arylsulfonate cyanine fluorescent dyes are described in Mujumdar et al. (1993) *Bioconjugate Chemistry*, 4:105-111; Southwick et al. (1990) *Cytometry*, 11:418-430; and U.S. Pat. No. 5,268,486. Cy5 is described in each of the references and is commercially available from Biological Detection Systems, Inc., Pittsburgh, Pa., under the tradename FLUOROLINK™ Cy5™. The arylsulfonate cyanine fluorescent dyes have high extinction coefficients (typically from 130,000 L/mole to 250,000 L/mole), good quantum yields, fluorescent emission spectra in a range (500 nm to 750 nm) outside of the autofluorescence wavelengths of most biological materials and plastics, good solubilities, and low non-specific binding characteristics.

Despite these excellent properties, arylsulfonate cyanine fluorescent dyes suffer from certain limitations. In particular, these dyes have a relatively narrow Stokes shift which results in significant overlap between the excitation and emission spectra of the dye. The overlap of excitation and emission spectra, in turn, can cause self-quenching of the fluorescence when the dye molecules are located close to each other when excited. Such self-quenching limits the number of arylsulfonate dye molecules which can be conjugated to a single antibody molecule for use in immunoassays. In the case of Cy5, an exemplary arylsulfonate cyanine fluorescent dye, the Stokes shift is 17 nm (which is the difference between an excitation wavelength of 650 nm and an emission wavelength of 667 nm). Optimal fluorescent yield is obtained when from two to four Cy5 molecules are conjugated to a single antibody molecule. The fluorescent signal output drops rapidly when more than four dye molecules are conjugated to a single antibody molecule. The inability to conjugate more than four dye molecules to individual antibody molecules significantly limits the sensitivity of immunoassays using Cy5-labelled antibodies and other binding substances.

There is a need for an improved optical detection system and an improved method for detecting analytes with high sensitivity by fluorescent immunoassay. The system and method should be easy to handle by the users and provide high specific signal and minimal background noise.

SUMMARY OF INVENTION

The present invention is directed to a fluorescent detection system for measuring a fluorescent signal on a probe tip. The system comprises: (a) a probe having an aspect ratio of length to width at least 5 to 1, the probe having a distal end and a proximal end, the proximal end having a sensing surface bound with a fluorescent label; (b) a light source for emitting excitation light directly to the probe's sensing surface; (c) a collecting lens pointed toward the sensing surface; and (d) an optical detector for detecting the emission fluorescent light; where the collecting lens collects and directs the emission fluorescent light to the optical detector.

The present invention is also directed to methods for detecting analytes by a fluorescent immunoassay. In one embodiment (three-step binding), the method comprises the steps of: (a) obtaining a probe having a first antibody immobilized on the tip of the probe, wherein the diameter of the tip surface is ≤5 mm; (b) dipping the probe tip into a sample vessel containing a sample solution having an analyte, moving the probe tip up and down and flowing the sample solution laterally in the sample vessel; (c) dipping the probe tip into a reagent vessel containing a reagent solution comprising a second antibody molecules conjugated with a first member of a binding pair, moving the probe tip up and down and flowing the reagent solution laterally in the reagent vessel; (d) dipping the probe tip into a washing vessel containing a wash solution; (e) dipping the probe tip into an amplification vessel containing an amplification solution comprising a polymer having a molecular weight of at least about 1 million Dalton and conjugated with at least 5 molecules of second member of the binding pair and at least 25 fluorescent labels, moving the probe tip up and down and flowing the amplification solution laterally in the amplification vessel to form an immunocomplex among the analyte, the first antibody, the second antibody, and the first and the second members of the binding pair on the probe tip; (f) dipping the probe tip into a second washing vessel containing a second wash solution; and (g) detecting the immunocomplex formed by detecting the fluorescent signal on the probe tip; wherein the first antibody and the second antibody are antibodies against the analyte.

The methods of the present invention achieves high sensitivity because the unique combination of (i) using a probe having a small sensing surface area for binding analyte molecules, (ii) moving the probe tip up and down and flowing the reaction solution laterally in a reaction vessel, and (iii) using a high molecular weigh polymer conjugated with multiple binding molecules and multiple fluorescent labels.

The present invention is further directed to a fluorescent labeling composition comprising: (a) a crosslinked FICOLL® (copolymers of sucrose and epichlorohydrin) having a molecular weight of at least 1 million Daltons, (b) at least 5 binding molecules, and (c) at least 25 fluorescent dye molecules, wherein the binding molecules and the fluorescent dye molecules are attached to the cross-linked FICOLL®.

BRIEF DESCRIPTION OF THE DRAWINGS

FIG. 13 illustrates an immunoassay format for detecting protein A. Ab: antibody, Ag: antigen (protein A), Sa: streptavidin, B: biotin, F: fluorescent label.

DETAILED DESCRIPTION OF THE INVENTION

Definitions

Figure 1:
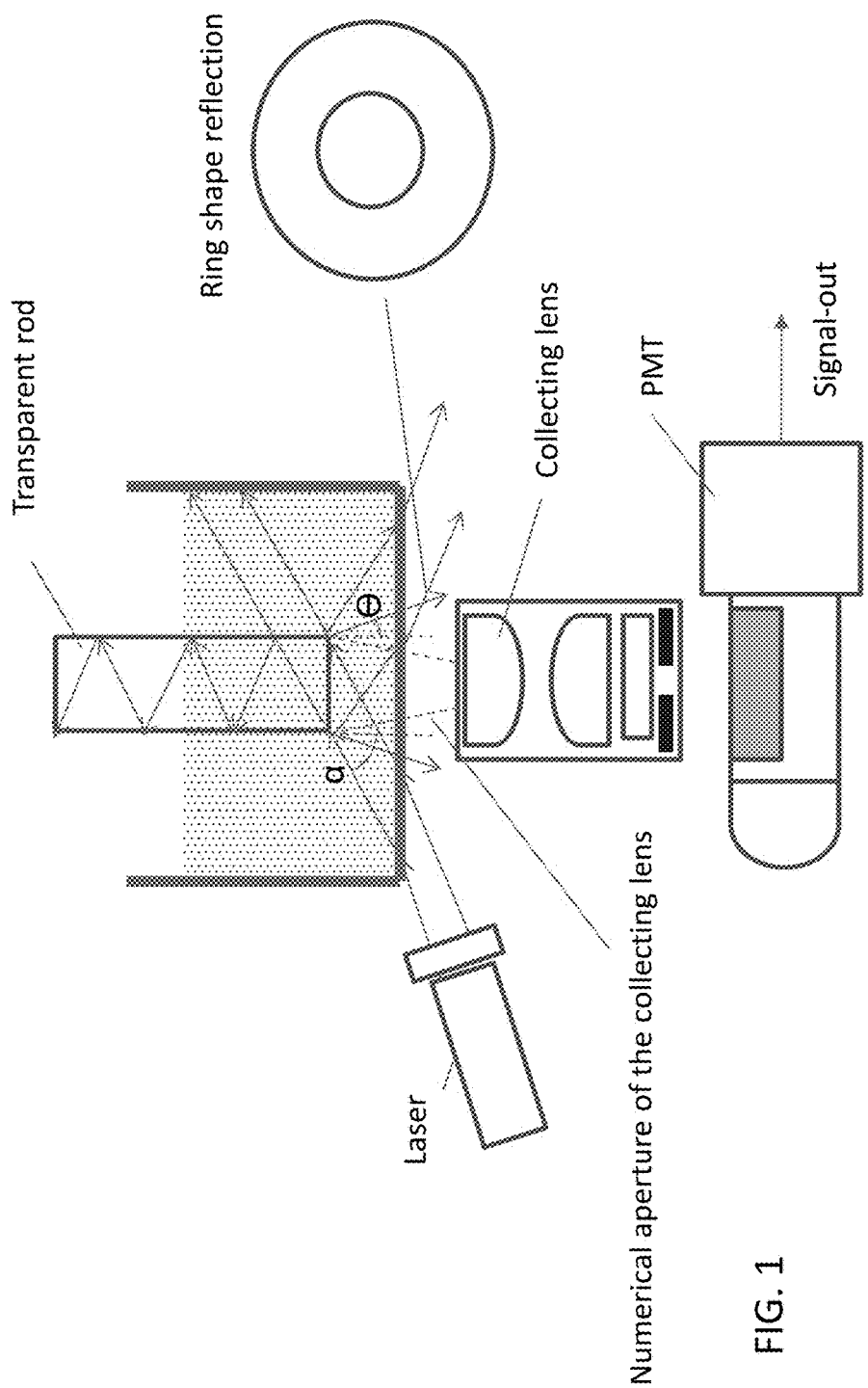
FIG. 1 illustrates a first embodiment of the optical detection system.

Terms used in the claims and specification are to be construed in accordance with their usual meaning as understood by one skilled in the art except and as defined as set forth below.

"About," as used herein, refers to within ±15% of the recited value.

An "analyte-binding" molecule, as used herein, refers to any molecule capable of participating in a specific binding reaction with an analyte molecule. Examples include but are not limited to, (i) antigen molecules, for use in detecting the presence of antibodies specific against that antigen; (ii) antibody molecules, for use in detecting the presence of antigens; (iii) protein molecules, for use in detecting the presence of a binding partner for that protein; (iv) ligands, for use in detecting the presence of a binding partner; or (v) single stranded nucleic acid molecules, for detecting the presence of nucleic acid binding molecules.

An "aspect ratio" of a shape refers to the ratio of its longer dimension to its shorter dimension.

A "binding molecular," refers to a molecule that is capable to bind another molecule of interest.

"A binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, lectin and carbohydrates. Preferred binding pairs are biotin and streptavidin, biotin and avidin, fluorescein and anti-fluorescein, digioxigenin/anti-digioxigenin. Biotin and avidin, including biotin derivatives and avidin derivatives such as streptavidin, may be used as intermediate binding substances in assay protocols employing complex binding sequences. For example, antibodies may be labeled with biotin ("biotinylated") and used to bind to a target substance previously immobilized on a solid phase surface. Fluorescent compositions according to the present invention employing an avidin or streptavidin may then be used to introduce the fluorescent label.

"Immobilized," as used herein, refers to reagents being fixed to a solid surface. When a reagent is immobilized to a solid surface, it is either be non-covalently bound or covalently bound to the surface.

"A monolithic substrate," as used herein, refers to a single piece of a solid material such as glass, quartz, or plastic that has one refractive index.

A "numerical aperture," as used herein, refers to a dimensionless number that characterizes the range of angles over which the system can accept or emit light.

"An optical fiber," as used herein, is a glass or plastic fiber that carries light along its length. An optic fiber is typically a circular cross-section dielectric waveguide consisting of a dielectric material (a core material) surrounded by another dielectric material with a lower refractive index (cladding).

A "probe," as used herein, refers to a substrate coated with a thin-film layer of analyte-binding molecules at the sensing side. A probe has a distal end and a proximal end. The proximal end (also refers to probe tip in the application) has a sensing surface coated with a thin layer of analyte-binding molecules.

Fluorescent Detection System

The present invention is directed to a fluorescent detection system for measuring a fluorescent signal on a probe tip. The inventors have discovered that by mounting both the light source and the detector at the proximal side of the sensing surface of the probe, the undesired reflection entering the detection optics is reduced and the detection efficiency is increased.

The system comprises: (a) a probe having an aspect ratio of length to width at least 5 to 1, the probe having a first end and a second end, the second end having a sensing surface bound with a fluorescent label; (b) a light source for emitting excitation light directly to the probe's sensing surface; (c) a collecting lens pointed toward the sensing surface; and (d)

an optical detector for detecting the emission fluorescent light; where the collecting lens collects and directs the emission fluorescent light to the optical detector The probe can be a monolithic substrate or an optical fiber. The probe can be any shape such as rod, cylindrical, round, square, triangle, etc., with an aspect ratio of length to width of at least 5 to 1, preferably 10 to 1. Because the probe is dipped in a sample solution and one or more assay solutions during an immunoassay, it is desirable to have a long probe with an aspect ratio of at least 5 to 1 to enable the probe tip's immersion into the solutions. Heterogeneous assays can be performed where the long probe is transferred to different reaction chambers. Dispensing and aspirating reagents and sample during the assay are avoided. The sensing surface of the probe is coated with analyte-binding molecules and bound with fluorescent labels.

Any light source that can emit proper excitation light for the fluorescent label is suitable for the present invention. A prefer light source is a laser that can emit light with wavelengths suitable for fluorescent labels. For example, the laser center wavelength is preferred to be 649 nm for Cy5 fluorescent dye. A suitable optical detector for detecting emission light is a photomultiplier tube (PMT), a charge coupled device (CCD), or a photodiode.

The light source and the optical detector including the collecting lens are mounted on the same side of the probe tip surface (the sensing surface). If the sensing surface faces down, they are both mounted below the tip surface. If the sensing surface faces up, they are both mounted above the tip surface. They are closer to the sensing surface than the other end of the probe. The sensing surface is always within the numeric aperture of the collecting lens. The probe can be, but does not have to be centrally aligned with the collecting lens.

FIG. 1 shows a first embodiment. An optically transparent rod (probe) is made from glass or quartz. The lower end of the rod is used as a sensing surface. Fluorescent labels are bond to the sensing surface. To detect the fluorescence, the rod's sensing end is immersed into a vessel with a clear bottom that contains a buffer solution optimized for fluorescent emission. The clear bottom's material may be selected from plastic, glass or quartz. An optical detector and an excitation laser are mounted on the same side of the vessel, and the collecting lens is underneath the sensing surface. The laser is aligned so that the laser beam projected onto the rod sensing surface at an incident angle $\alpha$, which is set greater than the rod's numerical aperture angle $\theta$. Because the rod's refractive index is much greater than the air and closer to that of the buffer solution, a large portion of the incident laser light will pass through the rod. A smaller amount of the laser light is reflected at the sensing surface. Some laser light is coupled into the rod and then reflected back from the other end of the rod. When $\alpha>\theta$, the reflected light exits the rod's sensing surface to form a ring shaped light band. The center of this ring has much lower light intensity. As the collecting lens is placed in the middle of the ring, the undesirable reflection entering the detection optics is reduced. To further decrease this reflection, the upper end of the rod can be tapered and sanded to certain roughness. To detect the emission at the sensing surface, a photo multiplier tube or CCD can be used. The distance between the rod's sensing surface and the collecting lens is adjustable to achieve the best detection efficiency.

Figure 2:
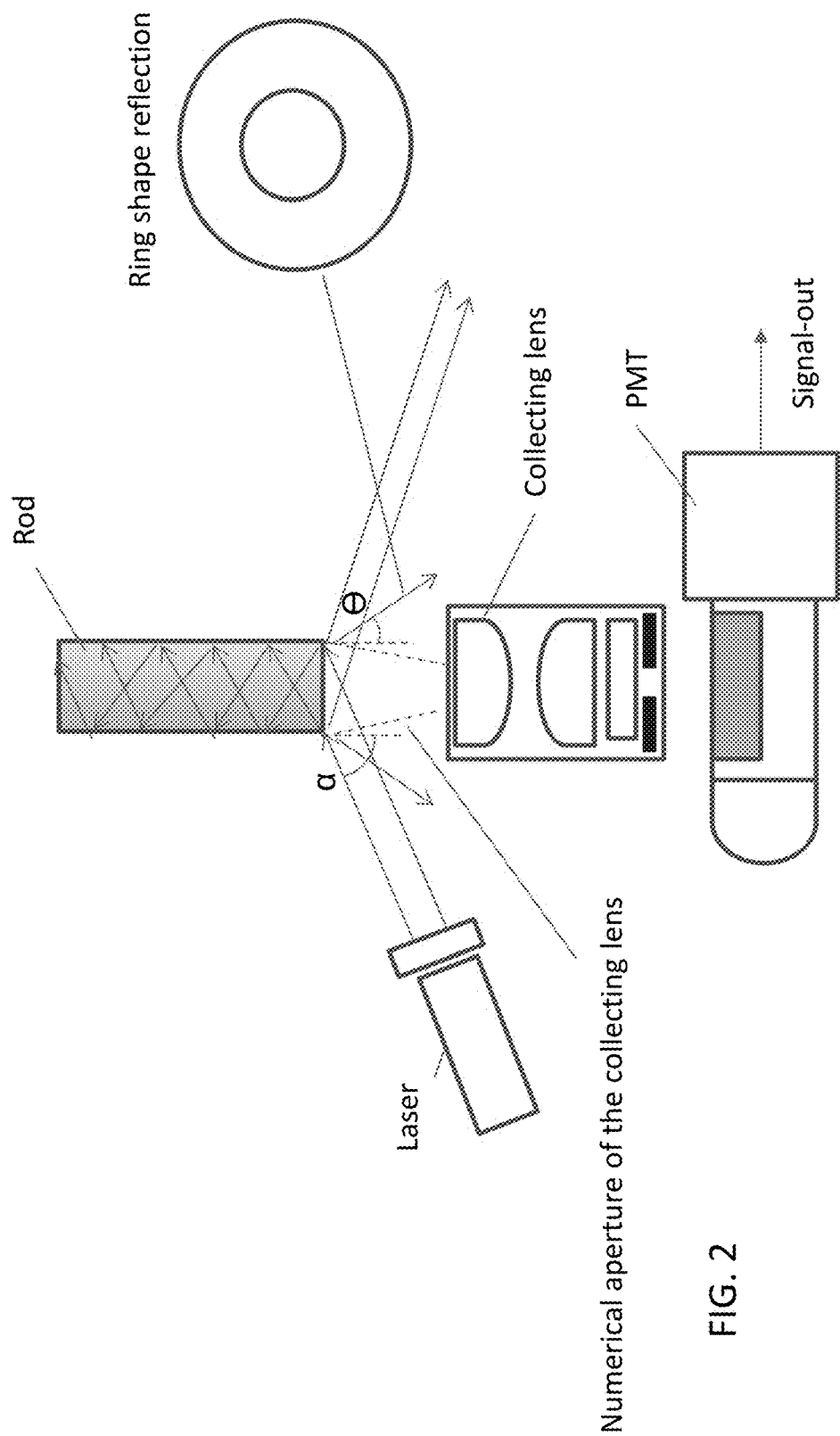
FIG. 2 illustrates a second embodiment of the optical detection system.

FIG. 2 shows a second embodiment where the rod is measured in air instead of in a buffer solution contained in a vessel. The configuration of the laser and the detector is similar to the first embodiment, where an optical detection system and an excitation laser are mounted on the same side of the rod and the collecting lens is underneath the sensing surface. The laser is aligned so that the laser beam projected onto the rod sensing surface at an incident angle $\alpha$, which is set greater than the rod's numerical aperture angle $\theta$. Some incident laser light will pass through the rod. A great portion of the laser light is reflected at the sensing surface. The remaining laser light is coupled into the rod and then reflected back from the upper end of the rod. When $\alpha>\theta$, the reflected light exits the rod's sensing surface to form a ring shaped light band. The center of the ring has much lower intensity. As the collecting lens is placed in the middle of the ring, the undesirable reflection entering the detection optics is avoided. To further decrease this reflection, the upper end of the rod can be tapered and sanded to certain roughness. To detect the emission at the sensing surface, a photo multiplier tube or CCD can be used. The distance between the rod's sensing surface and the collecting lens is adjustable to achieve the best detection efficiency.

Figure 3:
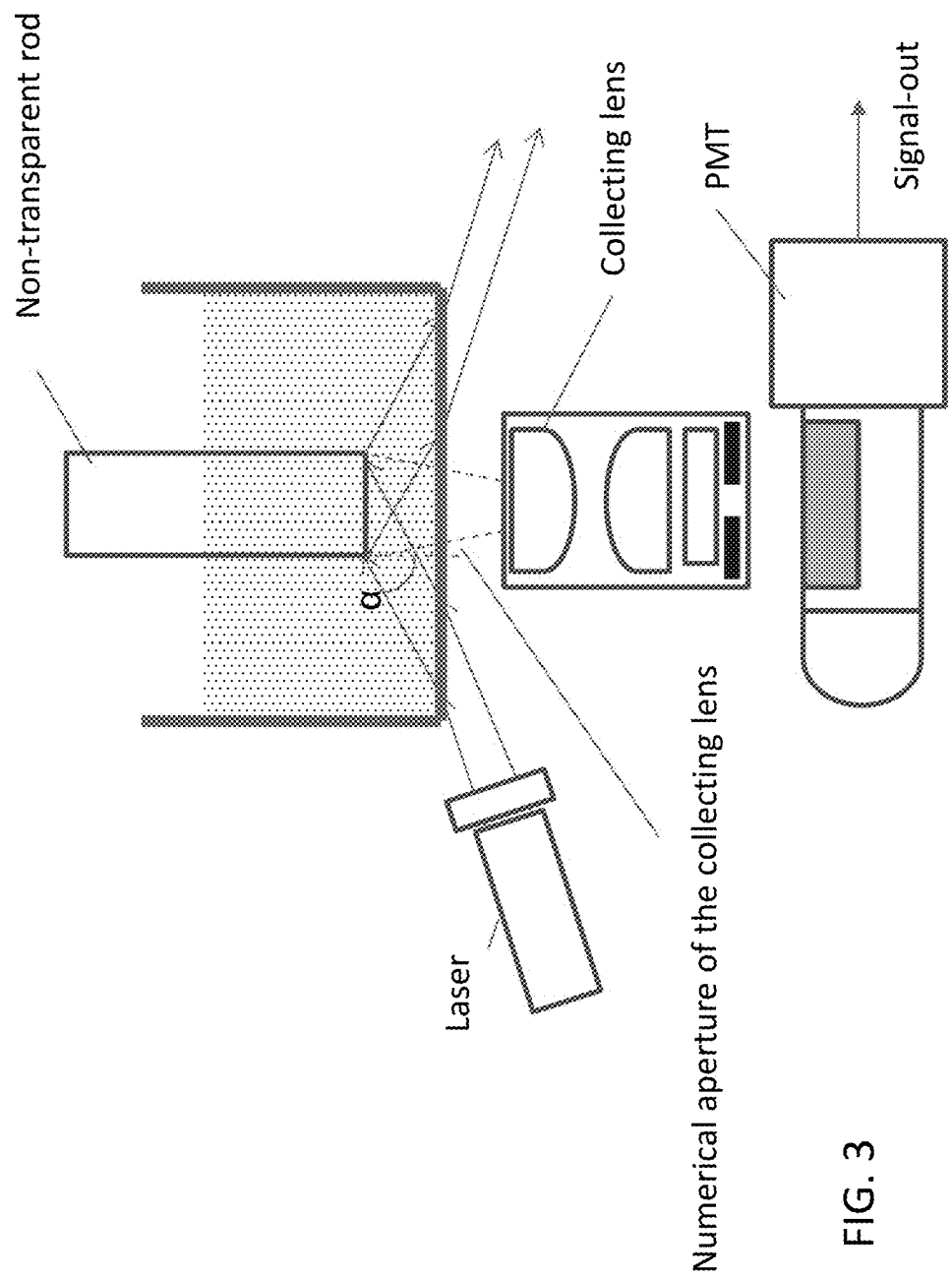
FIG. 3 illustrates a third embodiment of the optical detection system.

FIG. 3 shows a third embodiment that replaces the transparent rod of the embodiment in FIG. 1 with a non-transparent rod. The material of the non-transparent rod is possibly plastic, ceramics, and metals. The lower end of the rod is used as a sensing surface. To detect the fluorescence, the rod's sensing surface is immersed into a vessel with a clear bottom that contains a buffer solution optimized for fluorescent performance. The clear bottom's material may be selected from plastic, glass or quartz. An optical detection system and an excitation laser are mounted on the same side of the rod the vessel, and the collecting lens is underneath the sensing surface. The laser is aligned so that the laser beam projected onto the rod's sensing surface at an incident angle $\alpha$. Because the rod is non-transparent, the laser beam is reflected and absorbed at the sensing surface. It is preferred that the rod's material emits minimal fluorescence to the excitation laser. To detect the emission at the sensing surface, a photo multiplier tube or CCD can be used. The distance between the rod's sensing surface and the collecting lens is adjustable to achieve the best detection efficiency.

Figure 4:
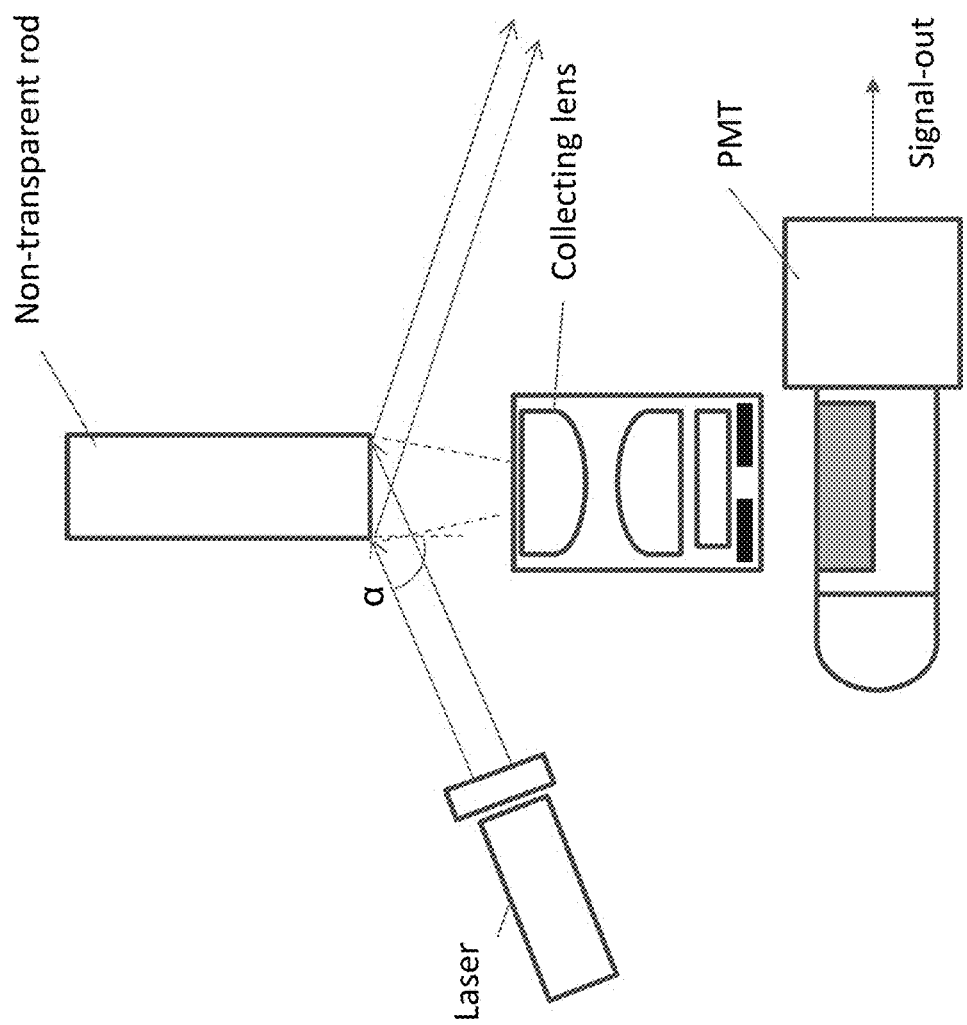
FIG. 4 illustrates a forth embodiment of the optical detection system.

FIG. 4 shows a fourth embodiment that has the non-transparent rod measured in air instead of in a buffer solution contained in a vessel. The material of the non-transparent rod is possibly plastic, ceramic, and metal. The lower end of the rod is used as a sensing surface. An optical detection system and an excitation laser are mounted on the same side the vessel, and the collecting lens is underneath the sensing surface. The laser is aligned so that the laser beam projected onto the rod's sensing surface at the incident angle $\alpha$. Because the rod is non-transparent, the laser beam is reflected and absorbed at the sensing surface. It is preferred that the rod's material emits minimal fluorescence to the excitation laser. To detect the emission at the sensing surface, a photo multiplier tube or CCD can be used. The distance between the rod's sensing surface and the collecting lens is adjustable to achieve the best detection efficiency.

Figure 5:
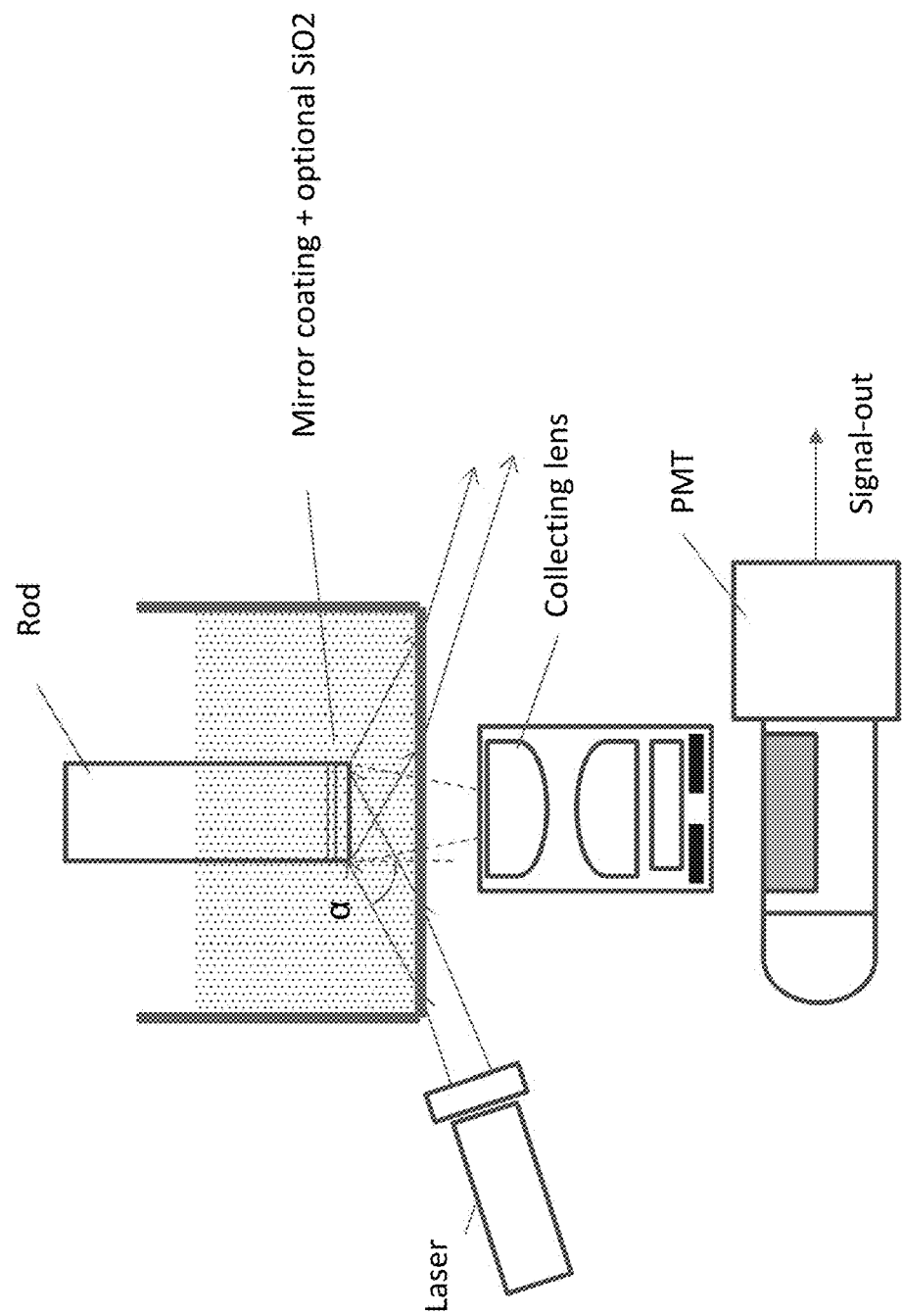
FIG. 5 illustrates a fifth embodiment of the optical detection system.

FIG. 5 shows a fifth embodiment that has a mirror like thin-film coated on the sensing surface of the rod. The rod can be either transparent or non-transparent. The mirror-like thin film coating is used to reflect light, either excitation or emission. The mirror coating can use aluminum, gold or silver. A second thin-film of $SiO_2$ is optionally coated on top of the first thin-film. The material of the non-transparent rod can be plastic, ceramic, or metal. The material of the transparent rod is chosen among glass, quartz, or plastic. Fluorescent labels are bond to the sensing surface. To detect fluorescence, the rod's sensing end is immersed into a vessel with a clear bottom that contains a buffer solution optimized for fluorescent performance. The clear bottom's material can be selected from plastic, glass or quartz. An optical detection system and an excitation laser are mounted on the same side the vessel, and the collecting lens is underneath the sensing surface. The laser is aligned so that the laser beam projected onto the rod's sensing surface at an incident angle α. Because the rod's sensing surface is coated with a first mirror thin film, the laser beam is reflected at a reflection angle α. To detect the emission at the sensing surface, a photo multiplier tube or CCD can be used. The distance between the rod's sensing surface and the collecting lens is adjustable to achieve the best detection efficiency.

Figure 6:
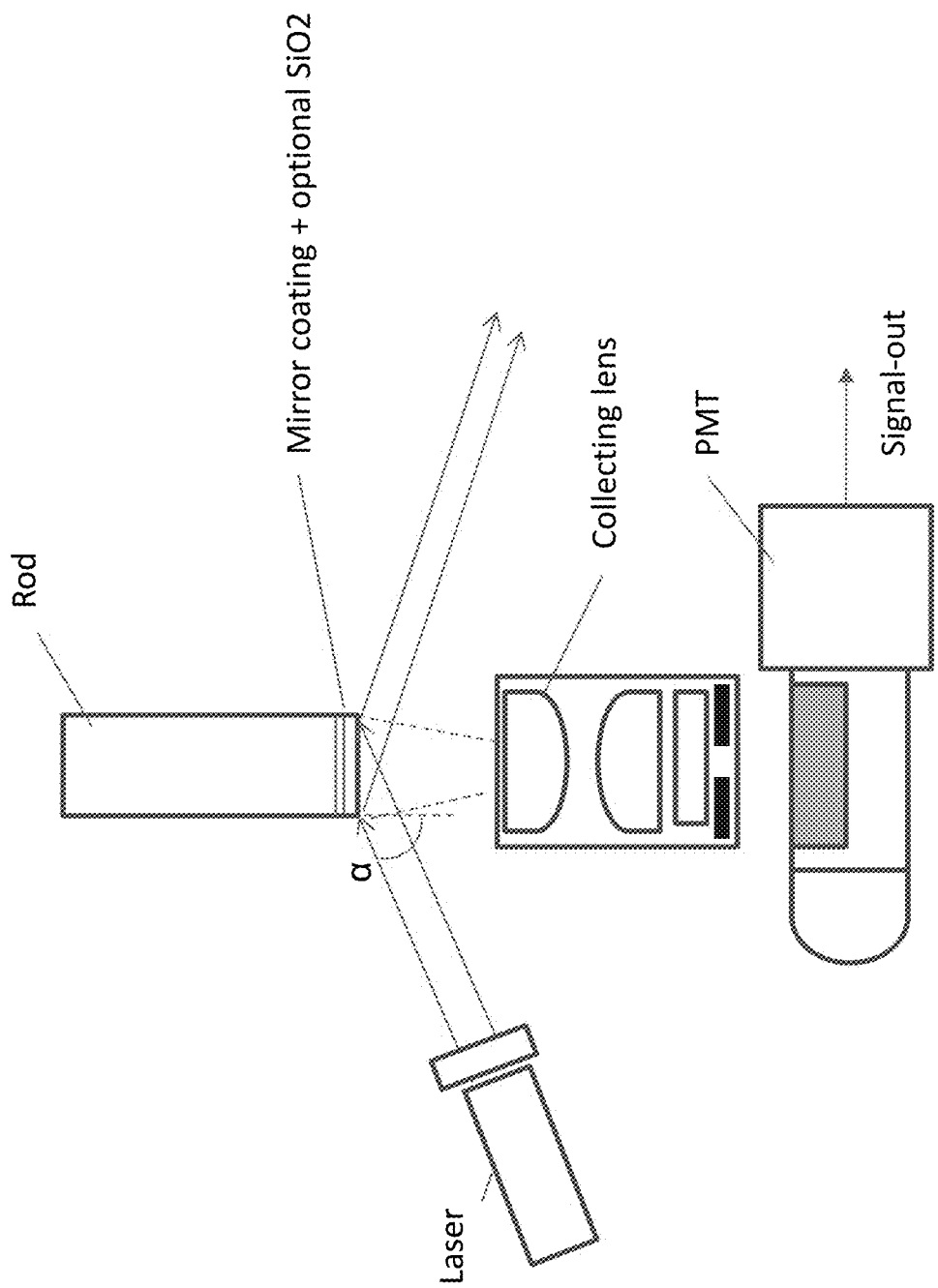
FIG. 6 illustrates a sixth embodiment of the optical detection system.

FIG. 6 shows a sixth embodiment that uses a mirror like thin-film coating on the sensing surface of the rod, but the measurement is done in air. The rod can be either transparent or non-transparent. The mirror-like thin film coating is used to reflect light, either excitation or emission. The mirror coating can use aluminum, gold or silver. Another thin-film of $SiO_2$ is optionally coated on top of the first mirror thin film. The material of the non-transparent rod is possibly plastic, ceramic, and metal. The material of the transparent rod is chosen from glass, quartz, or plastics. Fluorescent labels are bond to the sensing surface. To detect the fluorescence, the rod's sensing end, an optical detection system and an excitation laser are mounted on the same side of the rod's sensing surface, and the collecting lens is underneath the sensing surface. The laser is aligned so that the beam projected onto the rod's sensing surface at an incident angle α. Because the rod's sensing surface is coated with a mirror thin film, the laser beam is reflected. To detect the emission at the sensing surface, a photo multiplier tube or CCD can be used. The distance between the rod's sensing surface and the collecting lens is adjustable to achieve the best detection efficiency.

Although FIGS. 2, 4, and 6 are illustrated in a way that the laser and the optical detector are mounted below the probe tip, it should be understood that the probe can be flipped upside down and the laser and the optical detector can be mounted above the sensing surface to detect the fluorescent signal.

Detecting an Analyte by a Fluorescent Immunoassay

The present invention is also directed to methods of detecting an analyte in a liquid sample by a fluorescent immunoassay. The inventors have discovered that the combination of (i) using a probe having a small sensing surface area for binding analyte molecules, (ii) moving the probe tip up and down and flowing the reaction solution laterally in a reaction vessel, and (iii) using a high molecular weigh polymer conjugated with at least 5 binding molecules and at least 25 fluorescent labels, improves the sensitivity of detection level to pg/mL.

Figure 7:
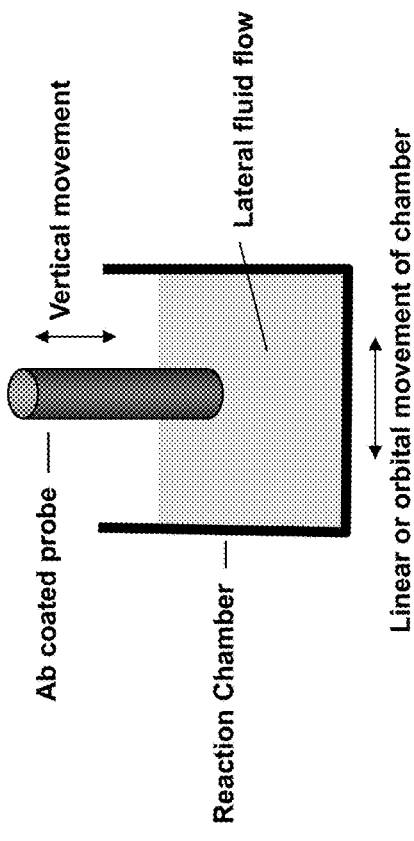
FIG. 7 illustrates the two-step binding method for detecting an analyte.
Figure 7:
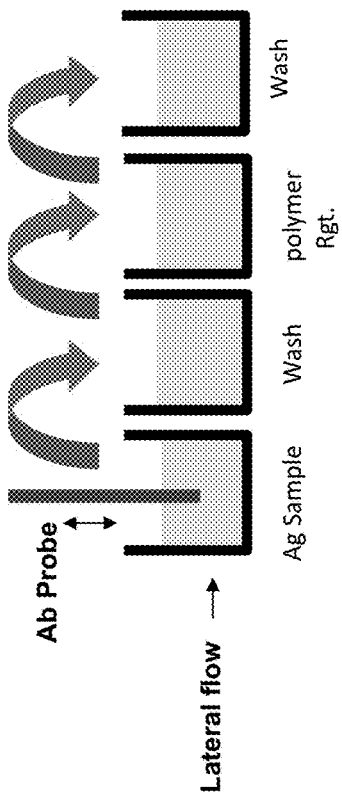

FIG. 7 illustrates one embodiment of the methods. In this embodiment (two-step binding), the method comprises the steps of: (a) obtaining a probe having a first antibody immobilized on the tip (sensing surface) of the probe, wherein the diameter of the tip surface is ≤5 mm; (b) dipping the probe tip into a sample vessel containing a liquid sample having an analyte; (c) moving the probe tip up and down and flowing the reagent solution laterally in the sample vessel to bind the analyte with the first antibody; (d) dipping the probe tip into a reagent vessel containing a reagent solution comprising a polymer having a molecular weight of at least 1 million Daltons and conjugated with at least 5 second antibody molecules and at least 25 fluorescent labels; (e) moving the probe tip up and down and flowing the reagent solution laterally in the reagent vessel to form an immunocomplex of the analyte, the first antibody, and the second antibody on the probe tip; (f) dipping the probe tip into a washing vessel containing a wash solution, and detecting the immunocomplex formed by detecting the fluorescent signal on the probe tip; wherein the first antibody and the second antibody are antibodies against the analyte. In the above method, an optional washing step can be added after the binding step (c). This extra washing step may not be required because the amount of the carried-over solution is minimal due to a small binding surface area.

In another embodiment (two-step binding), the method comprises the steps of: (a) obtaining a probe having a first antibody immobilized on the tip of the probe, wherein the diameter of the tip surface is ≤5 mm; (b) dipping the probe tip into a sample vessel containing (i) a liquid sample having an analyte and (ii) a reagent solution comprising a polymer having a molecular weight of at least about 1 million Dalton and conjugated with at least 5 second antibody molecules and at least 25 fluorescent label; (c) moving the probe tip up and down in the sample vessel and flowing the reagent solution laterally to form an immunocomplex of the analyte, the first antibody, and the second antibody on the probe tip; (d) dipping the probe tip into a washing vessel containing a wash solution; and (e) detecting the immunocomplex formed by detecting the fluorescent signal on the probe tip; wherein the first antibody and the second antibody are antibodies against the analyte.

In yet another embodiment (three-step binding), the method comprises the steps of: (a) obtaining a probe having a first antibody immobilized on the tip of the probe, wherein the diameter of the tip surface is ≤5 mm; (b) dipping the probe tip into a sample vessel containing a sample solution having an analyte, moving the probe tip up and down and flowing the sample solution laterally in the sample vessel; (c) dipping the probe tip into a reagent vessel containing a reagent solution comprising a second antibody molecules conjugated with a first member of a binding pair, moving the probe tip up and down and flowing the reagent solution laterally in the reagent vessel; (d) dipping the probe tip into an amplification vessel containing an amplification solution comprising a polymer having a molecular weight of at least about 1 million Dalton and conjugated with at least 5 molecules of second member of the binding pair and at least 25 fluorescent labels, moving the probe tip up and down and flowing the amplification solution laterally in the amplification vessel to form an immunocomplex among the analyte, the first antibody, the second antibody, and the first and the second members of the binding pair on the probe tip; (e) dipping the probe tip into a second washing vessel containing a second wash solution; and (f) detecting the immunocomplex formed by detecting the fluorescent signal on the probe tip; wherein the first antibody and the second antibody are antibodies against the analyte. In the above method, optional washing steps can be added after the binding steps (b) and (c). The extra washing steps may not be required because the amount of the carried-over solution is minimal due to a small binding surface area.

Methods to immobilize reagents to the solid phase (the sensing surface of the probe tip) are common in immunochemistry and involve formation of covalent, hydrophobic or electrostatic bonds between the solid phase and reagent. Analyte-binding molecules can be directly immobilized on the sensing surface. Alternatively, analyte-binding molecules can be indirectly immobilized on the sensing surface through a binding pair. For example, anti-fluorescein can be first immobilized either by adsorption to the solid surface or by covalently binding to aminopropylsilane coated on the solid surface. Then the analyte-binding molecule that is labeled with fluorescein can be bound to the solid surface through the binding of fluorescein and anti-fluorescein (binding pair).

The methods of the present invention achieves high sensitivity because the unique combination of (i) using a probe having a small sensing surface area for binding analyte molecules, (ii) moving the probe tip up and down and flowing the reaction solution laterally in a reaction vessel, and (iii) using a high molecular weight polymer conjugated with multiple binding molecules and multiple fluorescent labels.

The first factor of the present invention is to use a probe that has a small tip for binding analytes. The tip has a smaller surface area with a diameter ≤5 mm, preferably ≤2 mm or ≤1 mm. The small surface of the probe tip endows it with several advantages. In a solid phase immunoassays, having a small surface area is advantageous because it has less non-specific binding and thus produces a lower background signal. Further, the reagent or sample carry over on the probe tip is extremely small due to the small surface area of the tip. This feature makes the probe tip easy to wash, and causes negligible contamination in the wash solution since the wash solution has a larger volume. Another aspect of the small surface area of the probe tip is that it has small binding capacity. Consequently, when the probe tip is immersed in a reagent solution, the binding of the reagent does not consume a significant amount of the reagent. The reagent concentration is effectively unchanged. Negligible contamination of the wash solution and small consumption of the reagents enable the reagent solution, the amplification solution, and the wash solution to be re-used many times, for example, 2-8 times.

However, binding reaction at the probe tip with a surface area is slow. When the probe tip is immersed in a solution, the ratio of binding surface area to solution volume is small, thus it demands a very long incubation time for target molecules to diffuse to the probe's sensing surface. The second factor in the invention to enhance sensitivity is to induce a lateral flow (orbital flow) of the solution across the probe tip, which accelerates the capture of target molecules by its binding partner immobilized to solid phase. For example, the reaction vessel can be mounted on an orbital shaker and the orbital shaker is rotated at a speed at least 50 rpm, preferably at least 200 rpm, more preferably at least 500 rpm, such as 500-1,000 rpm. Additionally, the probe tip is moved up and down and perpendicular to the plane of the orbital flow, at a speed of 0.01 to 10 mm/second, in order to induce additional mixing of the solution above and below the probe tip. The combination of small surface for low background and flow for more rapid target molecule capture produces high specific assay signals and low background noise, which are the determinants of analytical sensitivity.

The third factor in the invention to enhance sensitivity is the use of high molecular weight polymers labeled with multiple binding molecules and multiple fluorescent dyes. Fluorescent dyes have many practical advantages as labels in immunoassays; primarily they are very stable and easy to link to binding proteins. Fluorescent dyes have a major limitation in that they cannot generate a sufficient fluorescent signal to be employed for sensitive assays. Therefore, it is important to have multiple fluorescent dyes labeled on one polymer to increase the fluorescent signal. Many polymers such as dextran and FICOLL® and nucleic acid polymers are suitable as dye carriers. The fluorescent label can be attached directly to the polymer or it can be attached indirectly to the polymer through a binding molecule such as an antibody or streptavidin.

When the binding molecule is a polypeptide or protein, such as an antibody, the fluorescent label can covalently bind to it through a variety of moieties, including disulfide, hydroxyphenyl, amino, carboxyl, indole, or other functional groups, using conventional conjugation chemistry as described in the scientific and patent literature. Alternatively, antibodies can be biotinylated by known techniques (see Wilchek and Bayer, (1988) ANAL. BIOCHEM. 171:1-32) and linked to the fluorescent label via avidin/streptavidin molecules.

Covalent binding of the fluorescent label to a polynucleotide can be effected through a variety of moieties, including aldehyde, ketone, isothiocyanate, imidate, inosine, acyl, and alkyl, using conventional conjugation chemistry, while derivatization with biotin is taught in many references. (Leary et al. (1983) *Proc. Natl. Acad. Sci. USA* 80:4045-4049; WO86/02929; EP063 879; Langer et al. (1981) *Proc. Natl. Acad. Sci. USA* 78:6633-6637; and EP2009 996).

Exemplary techniques for binding arylsulfonate cyanine fluorescent dye labels to antibodies and other proteins are described in U.S. Pat. Nos. 5,268,486; 5,650,334; the contents of which are in incorporated herein by reference. Techniques for linking a preferred Cy5 fluorescent label to both antibodies and nucleic acids are described in a technical bulletin identified as Cat. No. A25000, published by Biological Detection Systems, Inc., Pittsburgh, Pa.

The methods of the present invention can be detected by the fluorescent detection systems as described above in this application, where the light source and the detector are mounted at the same side (the proximal side) of the sensing surface of the probe.

Figure 8:
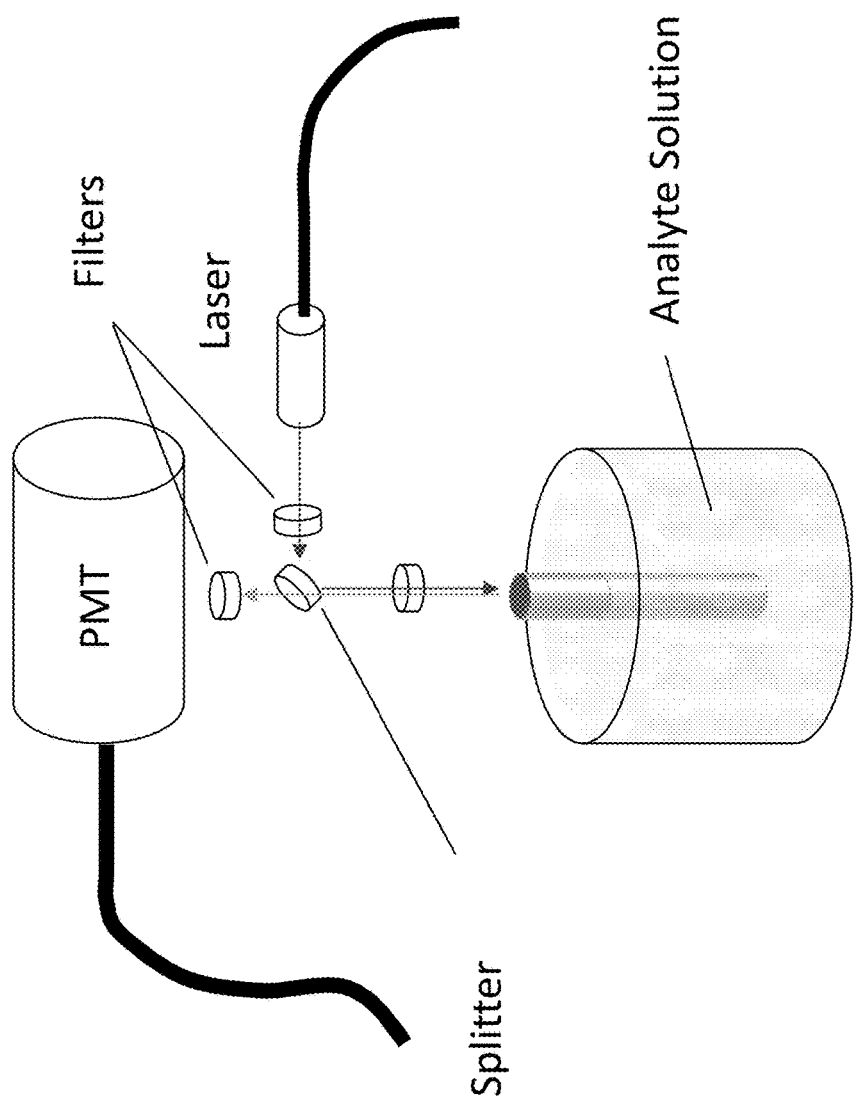
FIG. 8 illustrates an optical detecting system where the light source and the detector are both mounted at the side opposite to the sensing surface of the probe.
Figure 9:
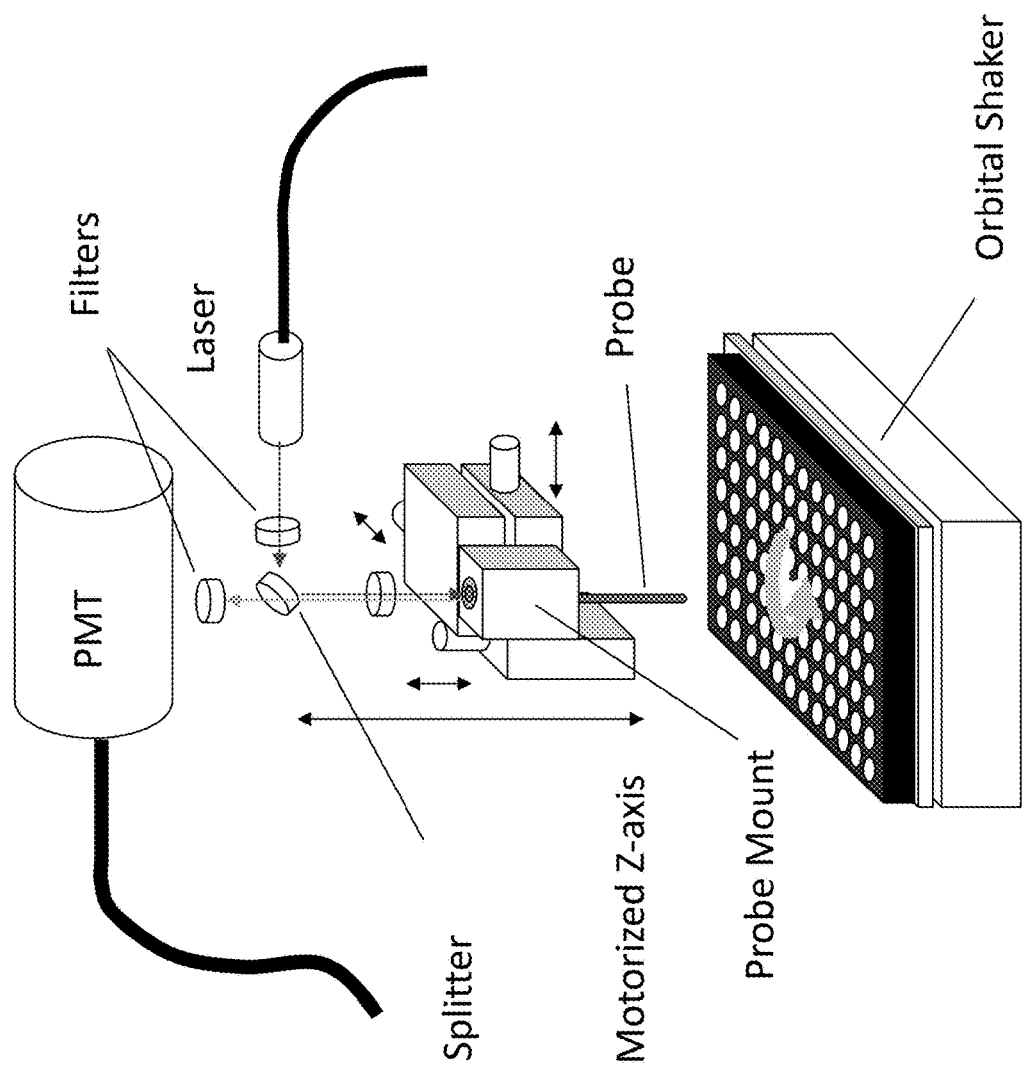
FIG. 9 illustrates another view of the optical detecting system where the probe is immersed into an analyte solution.

Alternatively, the methods of the present invention can be detected by an optical system where the light source and the detector are both mounted at the side opposite to the sensing surface of the probe, and close to the other end of the probe (FIG. 8-9)

In FIG. 8, the probe is removable from the detection system. The laser light is directly coupled into the one end of the probe. The probe can move in X-Y-Z directions in relative to the optical detection system. This motion allows the fine alignment between the probe and the optical detection system. The probe tip can be immersed into a well of a standard microtiter plate. The plate is mounted on an orbital shaker. The relative motion between the probe tip and the sample solution in the well increases the assay speed.

As shown in an enlarged drawing in FIG. 9, the probe's tip is directly immersed into the analyte sample for binding assays. The coupling end is detached from the optical detection system. A photo multiplier tube (PMT) is used as a photo detector.

The probe can be made of either a monolithic substrate or a fiber optic. If the probe is a fiber optic, then the fiber probe's coupling end can be coated with an anti-reflection coating layer to improve the coupling efficiency.

In one embodiment, a polarized filter is placed in front of the laser, and a second polarized filter with perpendicular polarization is placed in front of the PMT. With two polarized filters, the undesirable laser reflection is minimized.

In another embodiment, the polarized filters can be replaced with bandpass filters that only allow the fluorescent wavelength to pass.

The probe's core is greater than 0.1 mm in diameter, but no greater than 5 mm, preferably no greater than 2 mm, or 1 mm. A preferred numerical aperture is between 0.15 and 0.50.

High Molecular Weight Branched Polysaccharide Containing Multiple Binding Molecules and Fluorescent Labels.

The present invention is also directed to a fluorescent labeling composition comprising (a) a crosslinked FICOLL® having a molecular weight of at least 1 million Daltons, (b) at least 5 binding molecules, and (c) at least 25 fluorescent dye molecules, wherein the binding molecules and the fluorescent dye molecules are attached to the cross-linked FICOLL®. The composition preferably comprises 5-50 or 5-100 binding molecules and 25-100 or 25-500 fluorescent dye molecules.

In one embodiment, the fluorescent dye molecules are attached directly to the cross-linked FICOLL®. In another embodiment, the fluorescent dye molecules are attached indirectly to the cross-linked FICOLL® through the binding molecules such as antibody molecules or streptavidins. To minimize fluorescent quenching, the fluorescent dye molecules are attached to spaced-apart locations along the crosslinked FICOLL®.

This fluorescent labeling composition is a preferred composition for the above-described methods of the present invention.

FICOLL® is commercially available in 70K and 400K Dalton molecular weights. FICOLL® offers advantages for serving as a macromolecular carrier. One problem with crosslinking fluorescent protein in boosting assay sensitivity is that the non-specific, background signal can be increased. Specific assay signal and background signal increasing in the same proportion would result in the same signal to background ratio with no improvement in sensitivity. Polysaccharides in general exhibit negligible non specific binding to many of the solid phase materials commonly employed in immunoassays. Consequently, a FICOLL® macromolecular carrier increases the signal in specific binding while minimizing the non specific binding to the solid phase, therefore yielding an improvement in the signal to background ratio enhancing sensitivity.

FICOLL® is advantageous over an alternative polysaccharide dextran. Dextran, since it is linear with few branch points, is extremely polydisperse in its molecular weight distribution. In linking protein to polysaccharide carriers, reproducible results are obtained when starting material are of a defined, narrow molecular weight range. The branched structure of FICOLL® endows it with some tolerance to chemical cleavage or mechanical shearing and thus minimizing the impact on its molecular weight. The other aspect of the branched structure if FICOLL® is that it minimizes the interaction of the polymer with solid phase material used in immunoassay; consequently non-specific binding is lower compared to other polysaccharides.

FICOLL® 400 (molecular weight) is polydisperse and the vast majority of the material actually fractionates as much smaller molecules than IgG. The ideal polysaccharide carrier should have a molecular weight greater than one million Daltons, which elutes at or near the void volume of a Sepharose 4B CL column. Very little of the FICOLL® 400 preparation exhibits such high molecule weight polymers to be practically useful.

An aspect of the invention is to prepare crosslinked derivatives of FICOLL® to create high molecular weight polymers. The crosslinking of FICOLL® further increases the degree of branching within the polymer. An advantage of this aspect of the invention is that FICOLL® polymers can be prepared in a wide range of molecular weights by controlling the crosslinking chemistry. Crosslinked FICOLL® with molecular weights greater than one million Daltons can be achieved and those polymers remain soluble. Such polymers are capable of further derivatization for fluorescent dye and protein conjugation; the conjugated polymers exhibit signal amplification in solid phase binding assays, and most surprisingly, low non-specific binding to the solid phase. These performance features are not expected with commercial preparations of FICOLL® 400 or other polysaccharides.

The crosslinked FICOLL® compositions should have the following features: (a) soluble at greater than 2.5, 5 or 10 mg/ml; (b) mean hydrodynamic diameter greater than 100, 150, or 200 nm; (c) molecular weight greater than, 1, 2, 5, or 10 MD and (d) at least 25 functional groups per FICOLL® for attaching binding molecules and/or fluorescent dye molecules.

Figure 10:
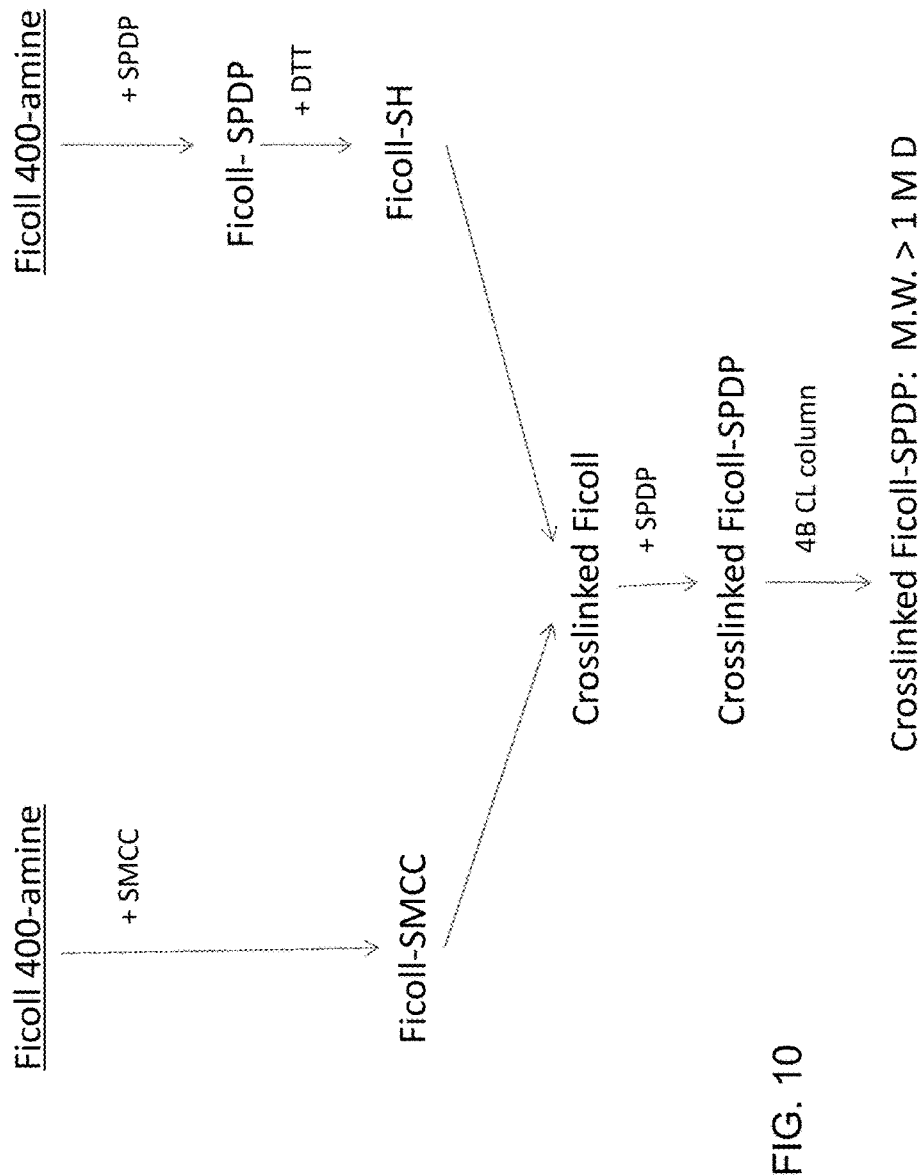
FIG. 10 illustrates a flow chart of preparing crosslinked FICOLL® 400.

Amine derivatives of FICOLL® are commercially available which enables crosslinking. FIG. 10 illustrates a flow chart for preparing crosslinked FICOLL®.

Figure 11:
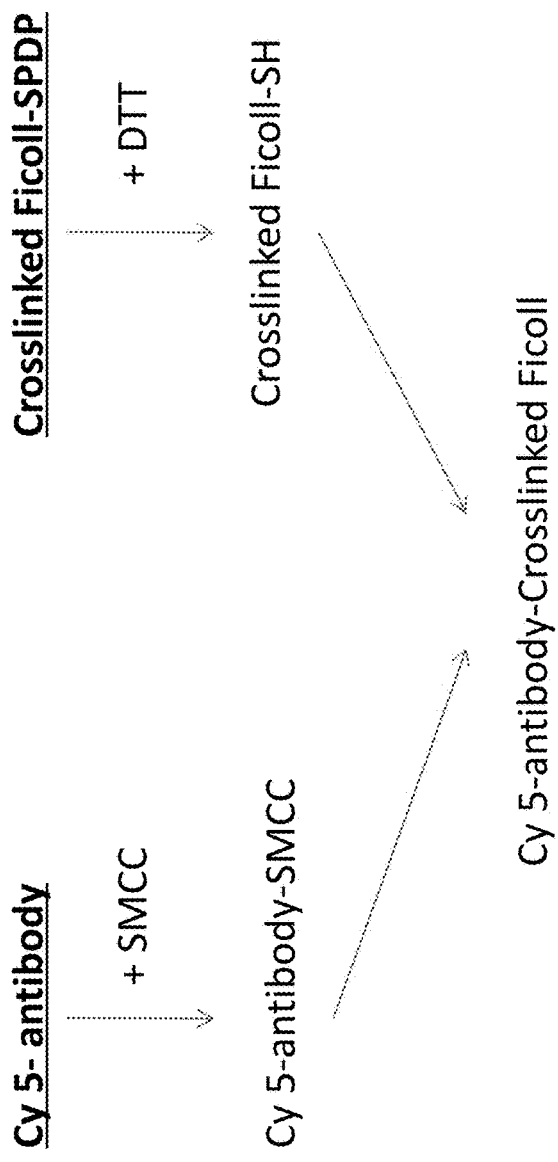
FIG. 11 illustrates a flow chart of preparing Cy 5-antibody-crosslinked FICOLL® 400.

Many fluorophores are commercially available as NHS derivatives that allow for coupling to the amine groups of proteins such as streptavidin or antibodies. Cy5 and Alexa Fluor 647 are good examples. The fluorescent labeled protein is then coupled to an amine derivative of FICOLL® by using the well established maleimide/thiol protein conjugation procedure or other crosslinking methods. FIG. 11 illustrates a flow chart for antibody conjugation to crosslinked FICOLL®.

Crosslinked FICOLL® can serve as a macromolecule carrier of Cy 5 anti-FITC and such a conjugate can be employed of boost immunoassay sensitivity compared to monomeric Cy 5-anti FITC.

The invention is illustrated further by the following examples that are not to be construed as limiting the invention in scope to the specific procedures described in them.

EXAMPLES

Example 1. Preparation of Crosslinked FICOLL® 400

FIG. 10 shows a flow chart of preparing crosslinked Ficoll 400.

To 2 ml of FICOLL® 400 (Sigma/Aldrich) that was aminated to contain 88 amines per FICOLL® 400 kD (Skold Technology) at 20 mg/ml in PBS was added 10 µL of SPDP (succinimydyl 6-[3-[2-pyridyldithio]-proprionamido] hexanoate, Invitrogen) at 50 mg/ml in DMF (N,N-Dimethylformamide). The SPDP to FICOLL® molecular coupling ratio (MCR) was 15. The mixture reacted for 1 hour at room temperature and followed by dialysis. Thiol incorporation was estimated to be 5.5 per FICOLL® 400 kD by standard methods.

To deprotect the thiols on SPDP-labeled FICOLL® 400, 30 µL of DTT (dithiotheritol, Thermo Scientific) at 38 mg/ml PBS was added to 20 mg in 1 ml PBS and allowed to react for two hours at room temperature. The SH-FICOLL® was purified on a PD10 column.

SMCC (succinimidyl 4[N-malemidomethyl]cyclohexan-1-carboxylate) was linked to aminated FICOLL® 400 (88 amines/-FICOLL®) in two preparations as follows: 1) Aminated Ficoll 400 at 10 mg in 1 ml PBS was mixed with 25 µL SMCC (Pierce Chemical) at 10 mg/ml DMF for a SMCC/FICOLL® MCR of 30. The mixture reacted for two hours at room temperature and followed by purification on a PD10 column (GE Healthcare). 2) Aminated FICOLL® 400 at 10 mg in 1 ml PBS was mixed with 12.5 µL SMCC at 10 mg/ml DMF for a SMCC/FICOLL® MCR of 15. The mixtures reacted for 2 hours at room temperature followed by purification on a PD10 column.

To crosslink the SH-FICOLL® 400 and SMCC-FICOLL® 400 two preparations were made: 1.) 10 mg in 1 ml PBS SH-FICOLL® 400 was mixed with 10 mg in 1 ml PBS SMCC-FICOLL® 400 (30 MCR). 2.) 10 mg in 1 ml PBS SH-FICOLL® 400 was mixed with 10 mg in 1 ml PBS SMCC-FICOLL® 400 (15 MCR). The mixtures reacted for overnight at 30° C.

To provide linking sites for antibody conjugation to the crosslinked FICOLL® 400, the residual amines were then reacted with an excess of SPDP. 20 mg of crosslinked FICOLL® 400 was mixed with 75 µL SPDP at 50 mg/ml DMF. The mixture reacted for 1 hour at room temperature followed by dialysis versus PBS.

Figure 12:
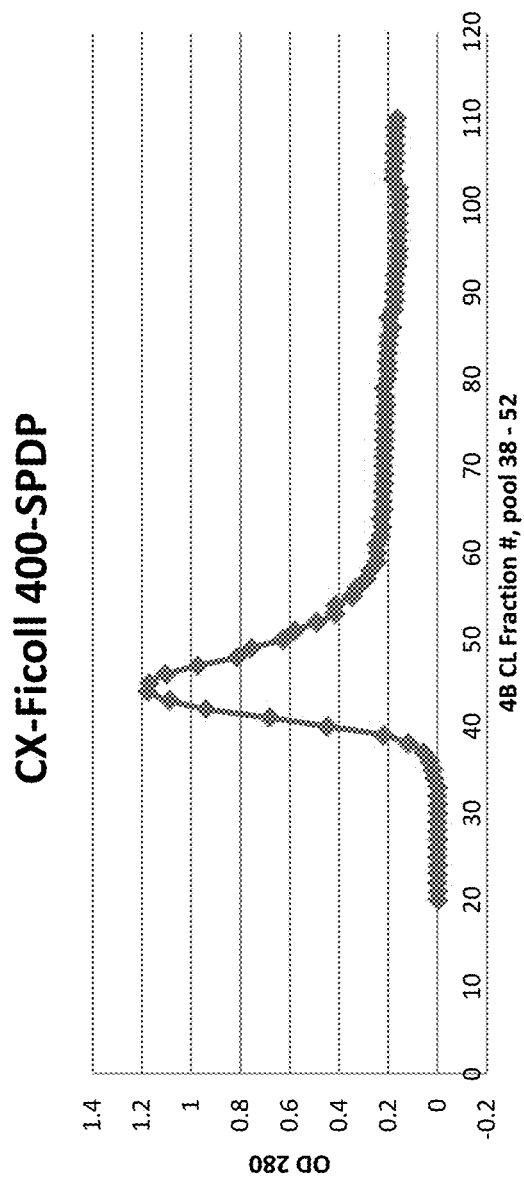
FIG. 12 illustrates the elution pattern of SPDP-labeled crosslinked FICOLL® 400 by Sepharose 4B CL chromatography.

The SPDP labeled crosslinked FICOLL® 400 preparations were then fractionated on a Sepharose 4B CL (GE Healthcare) column. The results show that the crosslinked FICOLL® are much larger polymers than the native FICOLL® 400, and the extent of crosslinking is dependent on the MCR of SMCC. High molecular weight polymers, which were eluted at fractions 40-50 with the peak at about fraction 45 eluting at or near the void volume of the 4B CL, were achieved with a SMCC MCR of 30 (FIG. 12); they are the preferred polymers for subsequent conjugation to binding proteins and fluorescent dye carrier. For comparison, the void fraction was fraction 32, and the non-crosslinked SPDP-FICOLL® was highly dispersed and eluted at fractions 50-120 with the peak at about fraction 98.

Example 2. Preparation of Cy5-Antibody-Crosslinked FICOLL® Conjugates

FIG. 11 shows a flow chart of preparing Cy 5-antibody-crosslinked FICOLL® 400. Anti FITC (Biospacific) at 3.2 mg/ml in 1 ml 0.1 M sodium carbonate pH 9.5 was mixed with 10.6 µl Cy5-NHS (N-Hydroxysuccinimide, GE Healthcare) at 10 mg/ml DMF and allowed to react for ½ hour at 30° C. The mixture was then purified on a PD 10 column. The Cy5-anti FITC at 1.5 mg/ml in 1 ml PBS was mixed with 1.9 µL SMCC at 5 mg/ml DMF and reacted for 1 hour at room temperature followed by purification on a PD 10 column.

The thiols on crosslinked FICOLL® 400-SPDP were deprotected by adding 30 µL DTT at 38 mg/ml to 0.7 mg crosslinked FICOLL® 400-SPDP in 1 ml PBS and reacting for 1 hour at room temperature followed by a PD 10 column to purify the crosslinked FICOLL®.

The Cy5-anti FITC-SMCC was mixed with crosslinked FICOLL® 400-SH and reacted overnight at room temperature. 10 µL NEM (N-ethyl-maleimide, Aldrich) at 12.5 mg/ml was then added and reacted for ½ hour at room temperature. The conjugate was then purified on a Sepharose 4B CL column.

Example 3. Preparation of Cy5-Antibody Dextran Conjugates

Cy5-antibody dextran (linear) conjugate (described in U.S. Pat. No. 5,650,334) was prepared for comparative studies.

Anti-FITC (Biospacific) at 3.2 mg/ml in 1 ml 0.1 M sodium carbonate pH 9.5 was mixed with 10.6 µL Cy5-NHS (GE Healthcare) at 10 mg/ml DMF and allowed to reacted for ½ hour at 30° C. The mixture was then purified on a PD 10 column.

The Cy5-anti FITC at 1.5 mg/ml in 1 ml PBS was mixed with 1.9 µL SMCC at 5 mg/ml DMF and reacted for 1 hour at room temperature followed by purification on a PD 10 column.

To thiolate dextran, 150 µL of a 34 mg/ml solution of succinimydyl 6-[3-[2-pyridyldithio]-proprionamido] hexanoate (LC-SPDP) (Pierce #21651) in DMF was added to a 5 ml solution containing 20 mg/ml aminodextran (Molecular Probes, #D-7145, 130 amines/dextran, 2000 kD M.W.) in PBS at pH 7.4. The reaction proceeded for 30 minutes at room temperature (RT), then the mixture was dialyzed overnight at RT against PBS. Greater than 95% of the amines in aminodextran were labeled with LC-SPDP during the reaction. The LC-SPDP-dextran was then purified on a Sepharose 4B CL column. To remove the low molecular weight dextran fragments, only the fractions of the void peak were collected.

A 6.15 ml solution of Cy 5-anti FITC at 2.6 mg/ml in PBS pH 7.4 was mixed with 156 of 2.7 mg/ml SMCC (Pierce #22320) in DMF and was allowed to react for 30 minutes at RT. Unreacted SMCC was removed by purification on a PD 10 column.

The LC-SPDP-dextran was reduced by adding 156 µL of 0.5M dithiothreitol to 5.2 ml of 3.1 mg/ml LC-SPDP-dextran and incubating for 15 minutes at RT. The dextran was then purified on a PD-10 (Pharmacia #17-0851-01) column.

Conjugation was achieved by mixing the reduced LC-SPDP-dextran with the SMCC-anti-FITC and incubating overnight at RT. NEM (Sigma #12828-7) was added at a final concentration of 1.0 mM to stop the reaction. The conjugate was then applied to a Sepharose 4B CL column and fractions eluting in the void volume were collected.

Example 4. Troponin I Assay Materials

Reaction disks made from PMMA plastic having benzophenone bovine serum albumin (BSA)-biotin immobilized on the bottom were prepared as follows. 100 µL benzophenone BSA-biotin per disk was then immobilized at 10 µL/ml by UV-curing for 60 minutes.

Streptavidin-monoclonal anti TnI conjugate (SA-anti TnI) was prepared using heterobifunctional linking reagents, S-acetylthioglycolic acid N-hydroxysuccinimide ester (SATA, Pierce #26102), and SMCC (Pierce #22320). Fifteen (15) molar excess of SATA (dissolved at 5 mg/mL in DMF) was reacted with 1 mg of anti-TnI (BioDesign) at 0.74 mg/mL in PBS at pH 7.4 for 3 hours at room temperature. Also, 15 molar excess of SMCC (dissolved at 5 mg/mL in DMF) was reacted with 1.1 mg of streptavidin at 1.1 mg/mL in PBS for 3 hours at room temperature. Unreacted linkers were removed from both anti TnI/SATA and streptavidin/SMCC reaction mixtures using a PD 10 column. The purified antiTnI-SATA and streptavidin-SMCC were mixed at the protein molar ratio of 1:3. The conjugation reaction was initiated by adding 1M hydroxylamine to a final concentration of 100 mM and incubated over 18 hours at 4° C. The reaction was stopped by adding 100 mM NEM (Aldrich Chemical) at a final concentration of 1 mM in the reaction mixture and incubating for 15 minutes at room temperature. After the incubation with NEM, mixture was purified using Sephacryl S 300 column (GE Healthcare).

40 µL of SA-anti-TnI at 25 µg/ml was added to each disks and incubated for 1 hour at room temperature. The assay buffer was PBS, 1% BSA, 0.1% Tween 20, pH 7.4. The disks were then washed 3 times.

Affinity purified goat anti-TnI peptide 3 (Biospacific) was labeled with fluorescein as follows: 1 mg of antibody in 1.8 ml PBS was mixed with 64 µL fluorescein-NHS (Invitrogen)

at 2 mg/ml DMF and reacted to 2 hours at room temperature followed by purification on a PD 10 column.

Example 5. Comparison of Cy 5-Anti FITC Vs. Cy 5-Anti FITC-Crosslinked FICOLL® in Troponin I Immunoassay Troponin I at 0, 10 and 50 ng/ml in 40 μL sample volumes were added to disks and incubated for 1 hour at room temperature. The disks were washed three times in assay buffer. 40 μL of fluorescein labeled anti-TnI peptide 3 at 10 μg/ml was added to each disk and incubated for 25 minutes at room temperature followed by three washes. 40 μL of either Cy5-anti FITC, Cy5-anti FITC-crosslinked (cx) FICOLL®, each at 10 μL/ml of antibody, was added to the disks with a 25 minute incubation at room temperature, followed the three washes. Cy5 fluorescence was then measured on the surface of each disk (Table 1).

TABLE 1

Assay Results

|  | Voltage | Voltage Background Corrected | Signal/Noise |
|---|---|---|---|
| Plastic Background | 0.9 | | |
| Cy5-Anti FITC | | | |
| TnI, 0 ng/ml | 1.01 | | |
| | 0.95 | | |
| av. | 0.98 | 0.09 | 1 |
| TnI, 10 ng/ml | 1.28 | | |
| | 1.18 | | |
| av. | 1.23 | 0.33 | 4.1 |
| TnI, 50 ng/ml | 2.68 | | |
| | 3.55 | | |
| av. | 3.11 | 2.21 | 27.6 |
| Cy5-Anti FITC-Cx-FICOLL ® | | | |
| TnI, 0 ng/ml | 1.02 | | |
| | 0.97 | | |
| av. | 0.99 | 0.09 | 1 |
| TnI, 10 ng/ml | 3.15 | | |
| | 3.15 | | |
| av. | 3.15 | 2.21 | 24.6 |
| TnI, 50 ng/ml | 8.95 | | |
| | 8.93 | | |
| av. | 8.94 | 8.04 | 89.3 |

Example 6. Comparison of Cy 5-Anti FITC-Crosslinked FICOLL® Vs. Cy 5-Anti FITC-Dextran in TnI Immunoassay Troponin I at 0 100 ng/ml in 40 μl sample volumes were added to disks and incubated for 1 hour at room temperature. The disks were washed three times in assay buffer. 40 μl of fluorescein labeled anti TnI peptide 3 at 10 μg/ml was added to each disk and incubated for 120 minutes at room temperature followed by three washes. 40 μL of either Cy5-anti FITC-Dextran (Example 3) or Cy5-anti FITC-crosslinked FICOLL® (Example 2), each at 10 ug/ml of antibody, was added to the disks with a 25 minute incubation at room temperature, followed the three washes. Cy5 fluorescence was then measured on the surface of each disk (see Table 2).

TABLE 2

Assay Results

|  | Voltage | Voltage Background Corrected | Signal/Noice |
|---|---|---|---|
| Plastic Background | 0.85 | | |
| Cy5-Anti FITC-Dextran | | | |
| TnI, 0 ng/ml | 4.71 | | |
| | 3.82 | | |
| av. | 4.25 | 3.4 | 1 |
| TnI, 100 ng/ml | 7.32 | | |
| | 7.61 | | |
| av. | 7.45 | 6.61 | 1.9 |
| Cy5-Anti FITC-Cx-FICOLL ® | | | |
| TnI, 0 ng/ml | 2.21 | | |
| | 2.3 | | |
| av. | 2.25 | 1.4 | 1 |
| TnI, 100 ng/ml | 8.5 | | |
| | 6.9 | | |
| av. | 7.7 | 6.85 | 4.9 |

Example 7. Preparation of Cy5-Streptavidin-Crosslinked FICOLL®

Cy 5 Labeling of Streptavidin

32 μL of Cy 5-NHS (GE Healthcare) at 5 mg/ml in DMF reacted with 1 ml of streptavidin (Scripps Labs) at 2.4 mg/ml in 0.1 M sodium carbonate buffer pH 9.5 for 40 minutes at 30° C. Applying the mixture to a PD 10 column (Pharmacia) removed unconjugated Cy 5. Spectral analysis indicated 2.8 Cy 5 linked per streptavidin molecule.

Conjugation of Cy 5-Streptavidin to Crosslinked FICOLL®

5.8 μL of SMCC (Pierce Chemical) at 10 mg/ml in DMF reacted with 2 mg streptavidin in 1 ml PBS pH 7.4 for 1 hour at room temperature. Applying the mixture to a PD 10 column removed unbound SMCC.

The thiols on crosslinked FICOLL® 400-SPDP were deprotected by adding 30 μL DTT at 38 mg/ml to 1 mg crosslinked FICOLL® 400-SPDP in 1 ml PBS and reacting for 1 hour at room temperature followed by a PD 10 column to purify the crosslinked FICOLL®.

The Cy5-streptavidin-SMCC was mixed with crosslinked FICOLL® 400-SH and reacted overnight at room temperature. 10 μL NEM (Aldrich) at 12.5 mg/ml was then added and reacted for ½ hour at room temperature. The conjugate was then purified on a Sepharose 4B CL column.

Example 8. Preparation of Cy 5 Labeled Crosslinked FICOLL® and Conjugation to Streptavidin The above methods (Examples 2, 3 and 7) require the binding protein to undergo two chemical modifications, one Cy 5 labeling and a second with SMCC to enable conjugation to crosslinked FICOLL®. In some cases particularly with antibodies, two chemical modifications may not be desirable since a loss in binding activity could result. The following method entails labeling crosslinked FICOLL® directly with Cy 5 followed by conjugation to the binding protein. The method therefore requires only a single chemical modification of the binding protein.

Preparation of Cy 5 Labeled Crosslinked-FICOLL®

To 2 ml of FICOLL® 400 (Sigma/Aldrich) that was aminated to contain 88 amines per FICOLL® 400 kD (Skold Technology) at 20 mg/ml in PBS was added 10 μL of SPDP (Invitrogen) at 50 mg/ml in DMF. The SPDP to FICOLL® molecular coupling ratio (MCR) was 15. The mixture reacted for 1 hour at room temperature followed by dialysis. Thiol incorporation was estimated to be 5.5 per FICOLL® 400 kD by standard methods.

To deprotect the thiols on SPDP labeled FICOLL® 400, 30 μL of DTT (Thermo Scientific) at 38 mg/ml PBS was added to 20 mg in 1 ml PBS and allowed to react for two hours at room temperature. The SH-FICOLL® was purified on a PD 10 column.

SMCC was linked to aminated FICOLL® 400 (88 amines/Ficoll) as follows: Aminated FICOLL® 400 (88 amines/FICOLL®) at 10 mg in 1 ml PBS was mixed with 25 μl SMCC (Pierce Chemical) at 10 mg/ml DMF for a SMCC/FICOLL® MCR of 30. The mixture reacted for two hours at room temperature followed by purification on a PD10 column To crosslink the SH-FICOLL® 400 and SMCC-FICOLL® 400, 10 mg of SH-FICOLL® 400 in 1 ml PBS was mixed with 10 mg in 1 ml PBS of SMCC-FICOLL® 400 (30 MCR). The mixture reacted for overnight at 30 C.

To provide linking sites for protein conjugation to the crosslinked FICOLL® 400, the residual amines were then reacted with SPDP at a MCR of 30. 20 mg of crosslinked FICOLL® 400 was mixed with 64 μl SPDP at 10 mg/ml DMF. The mixture reacted for 1 hour at room temperature followed by dialysis versus PBS. Modification with SPDP at a MCR of 30 leaves sufficient number to amino groups for subsequent labeling with Cy5-NHS. The SPDP labeled crosslinked FICOLL® 400 preparation was then fractionated on a Sepharose 4B CL (GE Healthcare) column.

For Cy 5 labeling, 15 μL of Cy 5-NETS at 5 mg/ml in DMF reacted with 1 mg SPDP-crosslinked FICOLL® in 1 ml 0.1 M sodium carbonate pH 9.0 for 1 hour at room temperature. The mixture was purified in a PD 10 column. Assuming the crosslinked FICOLL® had an average molecular weight of 4 million Daltons, spectral analysis showed about 45 Cy 5 incorporated per crosslinked FICOLL®. Antibody and streptavidin are typically labeled with about 2 Cy5.

Conjugation of Streptavidin to Cy 5-Crosslinked FICOLL®

5.8 μL of SMCC (Pierce Chemical) at 10 mg/ml in DMF reacted with 2 mg streptavidin in 1 ml PBS pH 7.4 for 1 hour at room temperature. Applying the mixture to a PD 10 column removed unbound SMCC.

The thiols on Cy 5-crosslinked FICOLL® 400-SPDP were deprotected by adding 30 DTT at 38 mg/ml to 0.7 mg crosslinked FICOLL® 400-SPDP in 1 ml PBS and reacting for 1 hour at room temperature followed by a PD 10 column to purify the crosslinked FICOLL®.

The streptavidin-SMCC was mixed with Cy 5-crosslinked FICOLL® 400-SH and reacted overnight at room temperature. 10 μL NEM (Aldrich) at 12.5 mg/ml was then added and reacted for ½ hour at room temperature. The conjugate was then purified on a Sepharose 4B CL column.

Example 9. Protein A Immunoassay

Probe Format

Probe Preparation

Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of murine monoclonal anti-fluorescein (Biospacific), 10 μg/ml in PBS at pH 7.4. After allowing the antibody to adsorb to the probe for 5 minutes, the probe tip was washed in PBS. The probe tip was then immersed in a solution containing affinity purified fluorescein labeled chicken anti-Protein A (Cygnus Technologies) at 10 μg/ml in PBS. The antibody was fluoresceinated by a standard method. After 10 minutes the probe tip was washed in PBS.

Protein A Immunoassay

The assay format is illustrated in FIG. 13.

The anti-Protein A coated probe tip was immersed in a microwell containing 200 μL Protein A samples diluted in assay buffer (PBS, 10 mg/ml BSA, 0.1% Tween 20). The microwells were positioned on an orbital mixer (Big Bear Automation) and with the probe held stationary, the microwell were moved at 250 rpm with a 2 mm diameter orbital stroke. After 30 minutes the probe tips were washed 3 times with PBS. The probe tips were then immersed in a microwell with 200 μL of biotin label affinity purified chicken anti-Protein A (Cygnus Technologies) at 10 μg/ml in assay buffer. The anti-Protein A was biotinylated by a standard method. After 5 minute incubation with orbital flow at 250 rpm, the probes were washed 3 times with PBS. The probe tips were them immersed in a microwell containing Cy5-streptavidin-crosslinked FICOLL® at 10 μg/ml in assay buffer. After five minute incubation at 250 rpm orbital flow, the probe tips were washed 3 times with PBS. Cy5 fluorescence bound to the probe tip was measured with the optics depicted in FIG. 1. Table 3 shows the results.

TABLE 3

| Assay Results Pro A | mV | | | Av. |
|---|---|---|---|---|
| 0 pg/ml | 93 | 92 | 87 | 91 |
|  | 78 | 78 | 76 | 73 |
|  | 77 | 108 | 96 | 94 |
|  | 112 | 109 | 85 | 102 |
|  | 62 | 65 | 57 | 61 |
|  | 98 | 108 | 104 | 103 |
|  |  |  | Av. | 87 |
| 10 pg/ml | 119 | 150 | 131 | 133 |
|  | 128 | 139 | 127 | 131 |
|  | 155 | 147 | 145 | 149 |
|  | 152 | 140 | 118 | 137 |
|  |  |  | Av. | 138 |
| 100 pg/ml | 349 | 376 | 364 | 360 |
|  | 317 | 320 | 293 | 310 |
|  |  |  | Av. | 335 |
| 1000 pg/ml | 1184 | 1167 | 1152 | 1168 |
|  | 1300 | 1447 | 1456 | 1401 |
|  | 1163 | 1146 | 1123 | 1144 |
|  | 1168 | 1004 | 1011 | 1061 |
|  | 1829 | 1312 | 1536 | 1559 |
|  | 1600 | 1124 | 1061 | 1262 |
|  |  |  | Av. | 1266 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A detection system for measuring a fluorescent signal in a fluorescent assay, comprising:

a probe having an aspect ratio of length to width at least 5 to 1, the probe having a distal end and a proximal end, the proximal end having a sensing surface bound with a fluorescent label;

a light source for emitting excitation light directly to the probe's sensing surface;

a collecting lens pointed toward the sensing surface; and an optical detector for detecting the emission fluorescent light; where the collecting lens collects and directs the emission fluorescent light to the optical detector.

2. The system according to claim 1, wherein the probe sensing surface has a diameter equal or less than 5 mm.

3. The system according to claim 1, wherein the probe is transparent.

4. The system according to claim 3, wherein the distal end of the probe is tapered and/or roughened to reduce undesired reflection.

5. The system according to claim 3, wherein the light source is aligned so that the light beam projected onto the sensing surface at an incident angle greater than the numerical aperture angle of the probe.

6. The system according to claim 3, wherein the probe is made of glass, quartz, or plastic.

7. The system according to claim 1, wherein the probe is a non-transparent monolithic rod.

8. The system according to claim 1, wherein the probe is made of plastic, ceramic, or metal.

9. The system according to claim 1, wherein the sensing surface is coated with a film selected from aluminum, gold, or silver, the film has a thickness from about 50 nm to about 500 µm.

10. The system according to claim 9, wherein a second film of $SiO_2$ is coated on top of the film of claim 9.

11. The system according to claim 1, further comprising a vessel containing a solution, wherein the proximal end of the probe is immersed in the solution, and the light source and the collecting lens are mounted on the bottom side of the vessel.

* * * * *